US010314794B2

(12) United States Patent
Gao et al.

(10) Patent No.: US 10,314,794 B2
(45) Date of Patent: Jun. 11, 2019

(54) METOPROLOL SUSTAINED-RELEASE COMPOSITION AND PREPARATION METHOD THEREOF

(71) Applicant: Institute of Pharmacology and Toxicology Academy of Military Medical Sciences P.L.A. China, Beijing (CN)

(72) Inventors: Chunsheng Gao, Beijing (CN); Yuli Wang, Beijing (CN); Meiyan Yang, Beijing (CN); Li Shan, Beijing (CN); Jingjing Dai, Beijing (CN); Yong Qian, Beijing (CN); Yan Qiu, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/320,200

(22) PCT Filed: Jun. 23, 2015

(86) PCT No.: PCT/CN2015/082033
§ 371 (c)(1),
(2) Date: Dec. 19, 2016

(87) PCT Pub. No.: WO2015/196956
PCT Pub. Date: Dec. 30, 2015

(65) Prior Publication Data
US 2017/0119701 A1    May 4, 2017

(30) Foreign Application Priority Data

Jun. 23, 2014 (CN) .......................... 2014 1 0283652

(51) Int. Cl.
A61K 31/138 (2006.01)
A61K 9/48 (2006.01)
A61K 9/50 (2006.01)
A61K 31/549 (2006.01)
A61K 9/16 (2006.01)

(52) U.S. Cl.
CPC .......... *A61K 31/138* (2013.01); *A61K 9/1676* (2013.01); *A61K 9/4808* (2013.01); *A61K 9/4858* (2013.01); *A61K 9/4866* (2013.01); *A61K 9/5042* (2013.01); *A61K 31/549* (2013.01)

(58) Field of Classification Search
CPC .. A61K 31/138; A61K 31/549; A61K 9/4808; A61K 9/1676
See application file for complete search history.

(56) References Cited

U.S. PATENT DOCUMENTS 5,516,531 A * 5/1996 Makino ................ A61K 9/1676
424/458
2007/0009589 A1* 1/2007 Raghupathi .......... A61K 9/2077
424/451

FOREIGN PATENT DOCUMENTS

| CN | 103142618 A | 6/2013 | |
| CN | 103655480 A | 3/2014 | |
| WO | WO-2005084636 A2 * | 9/2005 | ........... A61K 9/2081 |
| WO | WO-2014040548 A1 * | 3/2014 | ........... A61K 9/5042 |

OTHER PUBLICATIONS

Qian, Y. Translation of "Studies on Metoprolol Succinate Sustained Release Pellets Coated With Ethyl Cellulose and the Model Drug Itself as a Pore Former" May 2013, pp. 1-100 (Year: 2013).*
Machine translation of WO-2014040548-A1, 2018, pp. 1-8 (Year: 2018).*
Berglund, G. et al. "Low Doses of Hydrochlorothiazide in Hypertension" Europ. J. Clin. Pharmacol. 10, 177-182 (1976) (Year: 1976).*
Mayo Clinic "https://www.mayoclinic.org/diseases-conditions/high-blood-pressure/in-depth/diuretics/art-20048129" available Mar. 13, 2014 on archive.org, pp. 1-3 (Year: 2014).*
International Search Report (ISR) for PCT/CN2015/082033; I.A. fd: Jun. 23, 2015, dated Sep. 29, 2015, State Intellectual Property Office of the P.R. China, Beijing, China.
International Preliminary Report on Patentability (IPRP) including the Written Opinion of the International Searching Authority (PCT Rule 44bis) for PCT/CN2015/082033; I.A. fd: Jun. 23, 2015, dated Dec. 27, 2016, by the International Bureau of WIPO, Geneva, Switzerland.

(Continued)

*Primary Examiner* — Andrew S Rosenthal
(74) *Attorney, Agent, or Firm* — Sterne, Kessler, Goldstein & Fox P.L.L.C.

(57) ABSTRACT

The invention relates to a drug sustained-release composition, particularly a sustained-release composition comprising metoprolol and preparation method thereof. The invention also relates to a combination product comprising a sustained-release composition comprising metoprolol and a pharmaceutical composition comprising hydrochlorothiazide. The sustained-release composition comprising metoprolol according to the invention eliminates the phenomena of delayed release of such sustained-release compositions in the prior art, has a better drug release curve, and also have the advantages such as simple formula, easy operation, stable quality, strong controllability, and good reproducibility, and therefore have good application prospects.

17 Claims, 2 Drawing Sheets

(56) References Cited

OTHER PUBLICATIONS

Qian, Y., "Studies on metoprolol succinate sustained release pellets coated with ethylcellulose and the model drug itself as a pore former," Chinese Master's Theses Full-Text Database (Medicine and Health Sciences), No. 2, Feb. 15, 2014, ISSN: 1674-0246, pp. E079-45.

* cited by examiner

METOPROLOL SUSTAINED-RELEASE COMPOSITION AND PREPARATION METHOD THEREOF

TECHNICAL FIELD

The invention relates to a drug sustained-release composition, particularly a sustained-release composition comprising metoprolol and preparation method thereof. The invention also relates to a combination product comprising a sustained-release composition comprising metoprolol and a pharmaceutical composition comprising hydrochlorothiazide.

BACKGROUND ART

Cardiovascular disease is a class of diseases that greatly threaten human health. In recent years, with the continuous improvement of living standards, both the morbidity rate and mortality rate of the diseases show an upward trend all over the world. Hypertension, one of the most common cardiovascular diseases in the world, is a long term chronic disease, which can cause systemic arteriolospasm at early stage and atherosclerosis at late stage, and further cause lesions of important organs such as myocardial infarction, stroke and kidney failure, thereby seriously threatening human health and life. The prevalence rate of hypertension reaches about 10%, and even 20% in some developed countries. According to the statistics, there are more than 1 billion patients with hypertension in the whole world. China has become a country with a high morbidity rate of hypertension, and the morbidity rate has increased rapidly in recent 20 years. From now on, with the increasing pace of social life, the reducing of manual labor day by day, and the trend of diet towards high calories and high fats, an upward trend in the number of patients with hypertension will last for a long period.

In recent, calcium antagonists, β-receptor blockers, ACE inhibitors, and angiotensin antagonists are four main drugs in international antihypertensive drug market. Among them, β-receptor blocker is a best-selling drug that ranks second only to calcium antagonists such as amlodipine. Metoprolol succinate (1-isopropylamino-3-[p-(2-methoxyethyl)phenoxy]-2-propanol L(+)-succinate) (Formula I), the second generation β-receptor blocker antihypertensive drug, is highly selective for heart, is effective in reducing blood pressure, slowing heartbeat, improving myocardial ischemia, and improving heart function, and therefore is widely used in the treatment of hypertension, coronary disease, arrhythmia, and chronic cardiac insufficiency.

Hydrochlorothiazide (6-chloro-3,4-dihydro-2H-1,2,4-benzothiadiazine-7-sulfamide-1,1-dioxide, Formula II) is a diuretic. Thiazines influence resorption mechanism of electrolytes in kidney tubules, and increase excretion of sodium ion and chlorine ion. The diuretic effect of hydrochlorothiazide indirectly reduces blood plasma volume, accompanied by an increase in plasma renin activity, an increase in aldosterone system activity, an increase in $Na^+$—$K^+$ exchange, and a decrease in potassium in serum. The antihypertensive mechanism of thiazine diuretics is not clear yet, and it is generally believed that sodium excretion is primarily responsible for the antihypertensive effect. Thiazine diuretics can be used alone or in combination with other antihypertensive drugs, mainly for the treatment of primary hypertension. It is suggested in JNC 7 that hydrochlorothiazide is used as basic drug for antihypertensive treatment. When two drugs are used in combination, the combination of diuretic with one of ACEI, ARB and β receptor blockers is recommended. The dose of hydrochlorothiazide can be reduced when used in combination (Medical Research and Education, 2012, 29(2): 69-71).

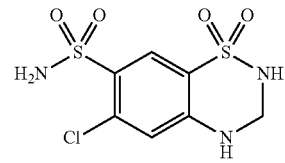

Formula II

The compound preparation of metoprolol succinate and hydrochlorothiazide exhibits a synergistic effect with respect to anti-hypertension. β receptor blockers reduce blood pressure by mediating the decrease in cardiac output and inhibiting the activity of renin. When β receptor blocker is used in combination with thiazine diuretic, the inhibition of aldosterone system activity is attenuated, and therefore their compound preparation exhibits a synergistic effect with respect to anti-hypertension. Moreover, the use of diuretic in combination enhances the effect of β receptor blocker in melanoderm and patients with low renin hypertension (*J Am Soc Hypertens,* 2010, 4(2): 90-98).

The patent (Publication No. CN103142618A) discloses a method for preparing a sustained-release capsule of metoprolol succinate and hydrochlorothiazide, wherein sustained-release pellet of metoprolol is prepared by pellet coating technique, the formula of the sustained-release coating is complex, and the coating formula is not reasonable enough. When water insoluble coating is used as coating material to prepare a sustained-release pellet, it has a good film-forming property but a poor permeability, and cannot ensure the release of active drug at an ideal release rate unless it is used in combination with other water soluble substance (referred to hereafter as pore-forming agent).

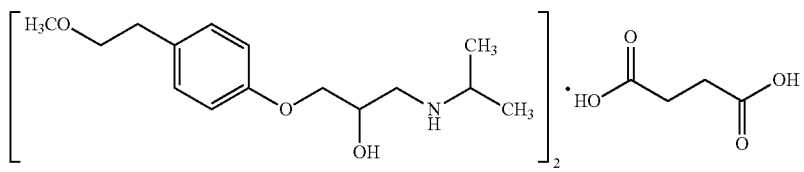

Formula I

However, when a pore-forming agent is a traditional hydrophilic polymer material, it can result in a lagging phase at early stage of drug release. When such a sustained-release preparation runs into gastrointestinal digestive juice upon oral administration, water permeates into the inside of pellet from outside through the controlled-release film, and has the drug dissolved; with gradual dissolution of the drug, the osmotic pressure increases gradually. When the osmotic pressure increases to a certain value, the drug diffuses through the film from inside to outside, i.e., drug release begins. Therefore, such sustained-release preparations cannot release drug immediately upon oral administration, and have to undergo a lagging phase of "moisture permeation, drug dissolution, and generation of osmotic pressure". Due to the delayed drug release of such sustained-release preparations, their therapeutic effect may be affected (*International Journal of Pharmaceutics*, 2011, 411:43-48). Therefore, there is still a demand in the art for a sustained-release composition comprising metoprolol, the preparation method of which is simple and the drug release of which is ideal.

Contents of Invention

After paying a lot of creative work, the inventors of the invention provide a sustained-release composition comprising metoprolol, the drug release of which is ideal and the preparation method of which is simple, and a combination product comprising the sustained-release composition and a pharmaceutical composition comprising hydrochlorothiazide, and thus accomplish the invention.

In a first aspect, the invention relates to a sustained-release composition comprising metoprolol, wherein said composition comprises a blank pellet core, an active constituent layer and a sustained-release coating layer, characterized in that said sustained-release coating layer comprises the active constituent, wherein said active constituent is selected from the group consisting of a free base of metoprolol, an optical isomer of metoprolol and a pharmaceutically acceptable salt of metoprolol.

In the invention, said pharmaceutically acceptable salt of metoprolol is selected from the group consisting of metoprolol succinate, tartrate, fumarate, sorbate, laurate, and hydrochloride.

The sustained-release composition according to any item of the first aspect of the invention, wherein said sustained-release coating layer comprises a sustained release material, the sustained release material may be any sustained-release material well known in the art, including, but not limited to: cellulose compound (e.g., ethyl cellulose), Eudragit NE 30D, Eudragit RS 30D, Eudragit RL30D or a mixture thereof, preferably ethyl cellulose having different viscosity, most preferably ethyl cellulose having a viscosity within a range of 9 mPa·s-22 mPa·s, such as Ethocel Standard 10 Premium.

The sustained-release composition according to any item of the first aspect of the invention, wherein said active constituent layer comprises or does not comprise an adhesive.

In the invention, said adhesive may be any adhesive well known in the art, including, but not limited to: one of starch paste, syrup, polyvinylpyrrolidone (povidone, PVP, such as PVP K30), methyl cellulose (MC), ethyl cellulose (EC), high-substituted hydroxypropyl cellulose (H-HPC), hydroxypropyl methyl cellulose (HPMC), carboxymethyl cellulose sodium, gelatin, and arabica acacia, or a mixture of two or more of them. If the active constituent layer comprises no adhesive, when a drug is loaded to a blank pellet core, the period of time for drug-loading is short, the drug-loading rate is high, and the drug can be provided in a constant release rate.

The sustained-release composition according to any item of the first aspect of the invention, wherein said sustained-release coating layer comprises the active constituent in a certain proportion, the active constituent comprised therein and optionally an additional pore-forming substance (e.g., hydroxypropyl cellulose) co-act as a pore-forming agent, i.e., the active constituent alone acts as a pore-forming agent, or the active constituent and an additional pore-forming substance (e.g., hydroxypropyl cellulose) co-act as a pore-forming agent.

In the invention, said additional pore-forming substance refers to a pore-forming agent other than the active constituent, including, but not limited to: polyethylene glycol, povidone, sucrose, salt, hydroxypropyl cellulose, hydroxypropyl methylcellulose, active drug, and the like or a mixture thereof. In an embodiment of the invention, said additional pore-forming substance is hydroxypropyl cellulose, preferably hydroxypropyl cellulose (HPC) having a viscosity within a range of 75 cpc-150 cpc, e.g., Klucel LF Type hydroxypropyl cellulose.

The sustained-release composition according to any item of the first aspect of the invention, wherein the sustained-release material and the pore-forming agent (i.e., the active constituent alone as a pore-forming agent or a combination of the active constituent and the additional pore-forming agent in the sustained-release coating layer) is in a weight ratio of 1:0.1~1:0.4, e.g., 1:0.1~1:0.3, e.g., 1:0.1~1:0.25, e.g., 1:0.1~1:0.225, e.g., 1:0.1~1:0.2, e.g., 1:0.1~1:0.15, e.g., 1:0.15~1:0.3, e.g., 1:0.15~1:0.25, e.g., 1:0.1~1:0.225, e.g., 1:0.1~1:0.2, e.g., 1:0.2~1:0.3, e.g., 1:0.2~1:0.25, e.g., 1:0.225~1:0.3, e.g., 1:0.225~1:0.25, e.g., 1:0.25~1:0.3, e.g., 1:0.25.

The sustained-release composition according to any item of the first aspect of the invention, wherein the active constituent and the additional pore-forming substance (e.g., hydroxypropyl cellulose) in the sustained-release coating layer is in a weight ratio of 1:3~3:1, e.g., 1:2~2:1, e.g., 1:1, e.g., 1:0.8.

The sustained-release composition according to any item of the first aspect of the invention, wherein the sustained-release coating causes a weight gain of 20%~60%, e.g., 30%~50%, e.g., 35%~45%.

The sustained-release composition according to any item of the first aspect of the invention, wherein the active constituent in the active constituent layer accounts for 40%~70%, e.g., 45%~65%, e.g., 50%~60%, e.g., 50%~55% of the total weight of the sustained-release composition.

The sustained-release composition according to any item of the first aspect of the invention, wherein said blank pellet core is well known in the art, which, for example, is selected from sucrose pellet core, starch pellet core, microcrystalline cellulose pellet core, or silica pellet core, etc. Said blank pellet core may be purchased from market, or prepared by conventional methods in the art such as method of extruding and round as ball and method of fluidized bed.

The sustained-release composition according to any item of the first aspect of the invention, wherein said blank pellet core has a particle size of 200 μm~900 μm, e.g., 200 μm~350 μm.

In the invention, said active constituent layer may further comprise an additional pharmaceutically acceptable adjuvant, which may, for example, be one or more selected from the group consisting of lubricant, surfactant, disintegrant, agent of aromatic taste, agent of sweet taste, anti-adherent and opacifier. Said lubricant includes, but is not limited to: sodium fumaryl stearate, sterotex, magnesium laurylsulfate, high melting-point wax, corn starch or a mixture thereof, preferably sodium fumaryl stearate. Said surfactant includes anion surfactant, cation surfactant, zwitterionic surfactant and nonionic surfactant. Said surfactant includes, but is not limited to: sodium lauryl sulfate, sodium hexadecyl sulfate, sodium octodecyl sulfate, sodium dodecyl benzene sulfonate, sodium dioctyl sulfosuccinate, sodium dihexyl sulfosuccinate, lecithin, sorbitan fatty acid ester, polyoxyethylene sorbitan fatty acid ester, polyoxyethylene aliphatate, polyoxyethylene aliphatic alcohol ether, oxyethylene-oxypropylene polymer, polyoxyethylene 40 stearate, polyoxyethylene 50 stearate, ethylene oxide triblock copolymer, propylene oxide triblock copolymer, sorbitan monopalmitate (Span-40), sorbitan monostearate (Span-60), glycerol monostearate, polyoxyethylene stearate, and the like, or a mixture thereof. Said disintegrant includes, but is not limited to: microcrystalline cellulose, low substituted hydroxypropyl cellulose sodium, cross-linked polyvinylpyrrolidone, sodium carboxymethyl starch, pregelatinized starch, alginic acid, starch, effervescence disintegrant, and the like, or a mixture thereof. Said anti-adherent includes, but is not limited to: talc, magnesium stearate, colloidal silicon dioxide, preferably talc. Said opacifier includes, but is not limited to: titanium dioxide and the like. Said agent of aromatic taste includes, but is not limited to: peppermint essence, lemon essence, orange essence, eudesmol, syringyl alcohol and the like. Said agent of sweet taste includes, but is not limited to: aspartame, vanillin, sorbitol, mannitol, artificial essence and the like.

In the invention, said sustained-release coating layer further comprise one or more selected from the group consisting of lubricant, plasticizer, anti-adherent, colorant, opacifier, agent of aromatic taste and agent of sweet taste. Said lubricant includes, but is not limited to: sodium fumaryl stearate, sterotex, magnesium laurylsulfate, high melting-point wax, corn starch or a mixture thereof, preferably sodium fumaryl stearate. Said plasticizer includes, but is not limited to: glycerol, propylene glycol, polyethylene glycol, glyceryl triacetate, triethyl citrate, phthalate, dibutyl sebacate, and the like, or a mixture thereof, preferably glyceryl triacetate. Said anti-adherent includes, but is not limited to: talc, magnesium stearate, colloidal silicon dioxide and the like, or a mixture thereof, preferably talc. Said opacifier includes, but is not limited to: titanium dioxide and the like. Said colorant includes, but is not limited to: ferrite yellow, iron oxide red, coccinellin, lemon yellow, sunset yellow, indigo blue and the like. Said agent of aromatic taste includes, but is not limited to: peppermint essence, lemon essence, orange essence, eudesmol, syringyl alcohol and the like. Said agent of sweet taste includes, but is not limited to: aspartame, vanillin, sorbitol, mannitol, artificial essence and the like, or a mixture thereof.

In the invention, said sustained-release composition is a sustained-release pellet.

In the invention, metoprolol in a unit preparation may be present in an amount of 1 mg~500 mg, preferably 5 mg~300 mg, more preferably 10 mg~250 mg, most preferably 20 mg~200 mg, further most preferably 23.75 mg~190 mg. In an embodiment of the invention, a unit preparation comprises metoprolol succinate in an amount of 23.75 mg. In another embodiment, a unit preparation comprises metoprolol succinate in an amount of 47.5 mg. In another embodiment, a unit preparation comprises metoprolol succinate in an amount of 95 mg.

A cumulative released percentage of the sustained-release composition according to any item of the first aspect of the invention reaches 1~30 wt % within 1 hour, reaches 30~55 wt % within 4 hours, reaches 50~85 wt % within 8 hours, and reaches nearly complete release, e.g., above 80 wt %, e.g., above 85 wt %, e.g., above 90 wt %, e.g., above 95 wt %, e.g., above 99 wt %, e.g., above 100 wt %, within 20 hours, wherein the cumulative released percentage is obtained on basis of the total weight of the sustained-release composition.

Compared to a conventional preparation or a conventional sustained-release preparation at a same dose, the relative oral bioavailability of the sustained-release composition according to any item of the first aspect of the invention is increased to 80%~120%, e.g., 85%~115%, e.g., 90%~110%. The time to peak ($T_{max}$) of the sustained-release composition according to any item of the first aspect of the invention is about 30 min in advance, compared to the reference preparation (Comparative example 1).

In a second aspect, the invention relates to a method for preparing the sustained-release composition according to any item of the first aspect of the invention, comprising the following steps of:

1) dissolving the active constituent and optionally an adjuvant of the active constituent layer in a suitable amount of a solvent to obtain a drug solution, and coating a blank pellet core with the drug solution to obtain a drug loaded pellet, and 2) dissolving a sustained-release coating material, the active constituent and optionally an additional pore-forming substance, as well as an adjuvant of the sustained-release coating layer in a solvent to obtain a solution, and coating the drug loaded pellet obtained in step 1) with the solution.

The method according to the second aspect of the invention, wherein the solvent is selected from the group consisting of water, ethanol, propanol, propylene glycol, chloroform and a mixture thereof. Said mixture is, for example, a mixture of water and ethanol.

In an embodiment of the invention, said method for preparing the sustained-release composition comprising metoprolol is as follows.

a. A sustained-release dose of an active constituent (free bases of metoprolol, optical isomers of metoprolol, or pharmaceutically acceptable salts of metoprolol) is dissolved in water to prepare a drug-containing coating solution at a concentration of 37.5% (w/v). Blank pellet cores are placed in a fluidized bed granulation coating device, and are coated with said drug-containing coating solution under stirring to obtain drug loaded pellets.

b. Ethyl cellulose as a sustained-release coating material is dissolved in an ethanol solution to obtain a concentration within a range of 5-12% (w/v), preferably within a range of 8-10% (w/v), and metoprolol is added in a corresponding dose, dissolved under stirring and heating, mixed homogeneously, and passed through a 100 mesh sieve, and then is atomized and sprayed onto the pellets loaded with metoprolol active constituent layer to perform sustained-release coating in the bottom-spray fluidized bed coating device, thereby obtaining a sustained-release composition comprising metoprolol.

The process parameters for drug-loading coating and sustained-release coating in the fluidized bed can be adjusted depending on practical conditions, the preferred process parameters are as follows.

For drug-loading coating, the temperature of air intake is 60~70° C. (the temperature in pan is kept within a range of 50±2° C.); the pressure of air intake is 0.3~0.5 bar; the pressure of atomization is 1.0~2.0 bar; and the rate of liquid-spraying is 5~15 g/min.

For sustained-release coating, the temperature of air intake is 40~45° C. (the temperature in pan is kept within a range of 30~35° C.); the pressure of air intake is 0.3~0.5 bar; the pressure of atomization is 1.0~2.0 bar; the rate of liquid-spraying is 3~12 g/min.

In a third aspect, the invention relates to a pharmaceutical composition, comprising the sustained-release composition according to any item of the first aspect of the invention, and optionally a pharmaceutically acceptable carrier or excipient.

In a fourth aspect, the invention relates to a combination product, comprising the sustained-release composition according to any item of the first aspect of the invention and a pharmaceutical composition comprising hydrochlorothiazide.

In the combination product according to the fourth aspect of the invention, said sustained-release composition comprising metoprolol and said pharmaceutical composition comprising hydrochlorothiazide can be capsulated into a capsule, or tableted into a tablet, wherein said tablet is, for example, a conventional tablet, double-layer tablet, chewable tablet or orally disintegrating tablet.

In an embodiment of the invention, said pharmaceutical composition comprising hydrochlorothiazide comprises an active agent hydrochlorothiazide, a filler and/or an adhesive, and may further comprise an additional pharmaceutically acceptable adjuvant, such as surfactant, disintegrant, agent of aromatic taste, agent of sweet taste, anti-adherent, opacifier and plasticizer.

The invention also relates to the sustained-release composition according to any item of the first aspect of the invention or the combination product according to any item of the third aspect of the invention, for use in the manufacture of a medicament for preventing or treating a disease such as hypertension, angina, myocardial infarction, hypertrophic cardiomyopathy, aortic dissection, arrhythmia, hyperthyreosis, and cardiac neurosis.

The invention also relates to a method for preventing or treating a disease such as hypertension, angina, myocardial infarction, hypertrophic cardiomyopathy, aortic dissection, arrhythmia, hyperthyreosis, and cardiac neurosis, comprising a step of administering to a subject in need thereof a prophylactically or therapeutically effective amount of the sustained composition according to any item of the first aspect of the invention or the combination product according to any item of the third aspect of the invention.

The invention also relates to the sustained-release composition according to any item of the first aspect of the invention or the combination product according to any item of the third aspect of the invention, for use in the prevention or treatment of a disease such as hypertension, angina, myocardial infarction, hypertrophic cardiomyopathy, aortic dissection, arrhythmia, hyperthyreosis, and cardiac neurosis.

The invention provides a sustained-release composition comprising metoprolol, consisting of the following three parts: a. a blank pellet core; b. an active constituent layer, i.e., a drug layer; and c. a sustained-release coating layer (FIG. 1), wherein the sustained-release coating layer comprises a certain proportion of an active constituent, i.e., metoprolol, that is, the active constituents are present in two forms, respectively, i.e., in the rapid-release part and the sustained-release part, respectively; and the active constituent of the rapid-release part of is present within the controlled-release film, thereby providing a certain drug-release rate at the early stage of release, eliminating the phenomena of delayed-release in the early state of release as commonly seen in conventional film-controlled sustained-release formulations of highly water soluble drugs (*International Journal of Pharmaceutics*, 2011, 411:43-48), and achieving an effective combination of rapid release and sustained release, and thus having a stable and ideal drug-release profile.

In addition, a certain dose of the active constituent in the sustained-release coating layer can also act as a pore-forming agent, so as to modulate the release of drug. Moreover, the active constituent can not only be used as a pore-forming agent by itself, but also be mixed with a pore-forming agent other than the active constituent in a certain proportion to co-act as a pore-forming agent, so as to better modulate the release of drug and obtain a more ideal drug release profile.

Furthermore, the presence of the active constituent in the sustained-release coating film can eliminate electrostatic adsorption during polymer film coating, to make the coating easily.

In addition, the technical solutions of the invention can reduce the use of adjuvants and effectively enhance the drug-loading amount of a preparation, thereby reducing the volume of the preparation so that the preparation is convenient for administration in a patient.

The sustained-release compositions according to the invention also have the advantages such as simple formula, easy operation, stable quality, strong controllability, and good reproducibility.

In the invention, the term "metoprolol" when used alone, if not specially specified, refers to metoprolol drug, e.g., free base of metoprolol, optical isomer of metoprolol or pharmaceutically acceptable salt of metoprolol.

In the invention, said free base of metoprolol refers to metoprolol that is present in a form of a free single molecule or a multi-molecular aggregate, rather than forming a salt with other organic or inorganic acid.

A person skilled in the art shall realize that metoprolol has a chiral center, said optical isomer of metoprolol according to the invention includes the R- or S-optical isomer. In an embodiment of the invention, said optical isomer of metoprolol has a certain optical purity, with an cc value of, e.g., above 50%, e.g., above 60%, e.g., above 70%, e.g., above 80%, e.g., above 90%, e.g., above 95%, e.g., above 98%, e.g., above 99%, e.g., above 99.9%, e.g., 100%.

In the invention, said sustained-release pellets or said pharmaceutical composition granules comprising hydrochlorothiazide have a particle size of 150 μm~1500 μm, e.g., 300 μm~1000 μm, e.g., 400 μm~850 μm, e.g., 610 μm~750 μm.

In the invention, the term "pharmaceutically acceptable" generally refers to being useful in pharmaceutical field, not harmful to product or mammal, or having a reasonable or acceptable benefit/risk ratio.

In the invention, the term "carrier" or "excipient" may be any conventional carrier and excipient in pharmaceutical field. The selection of a particular carrier and excipient depends on method of administration or type and state of a disease in a patient to be treated. A method for preparing a suitable pharmaceutical composition for use in a specific method of administration completely falls into the scope of knowledge mastered by a person skilled in the art. For example, pharmaceutically acceptable carrier or excipient include conventional carrier, excipient, diluent, filler, solvent, support agent, adhesive, moistening agent, disintegrant, absorption enhancer, surfactant, adsorption carrier, lubricant, and the like in pharmaceutical field. If necessary, agent of aromatic taste, preservative, agent of sweet taste, and the like may also be included.

In the invention, the term "subject" refers to a subject to which the sustained-release composition according to any item of the first aspect of the invention, the pharmaceutical composition according to any item of the third aspect or the combination product according to any item of the fourth aspect of the invention is administered. In an embodiment of the invention, said subject is mammal, such as human, canine, murine, feline, bovine, equine, or caprid; in a preferred embodiment, said subject is human.

In the invention, said sustained-release composition or combination product is preferably orally administered to a subject.

The administered amount of the sustained-release composition according to any item of the first aspect of the invention, the pharmaceutical composition according to any item of the third aspect or the combination product according to any item of the fourth aspect, depends on many factors, e.g., nature and severity of the disease to be prevented or treated, gender, age, body weight, sensitivity and individual response of a patient or animal, the particular compound used, administration route, administration frequency, the desired therapeutic effect, and the like. Said administered amount may be administered in a single dose or in several (e.g., two, three or four) separate doses. A single maximum dose is generally not greater than 30 mg/Kg body weight, e.g., 0.001-30 mg/Kg, preferably 0.01-5 mg/Kg, and a better dose range is 0.5-2 mg/Kg body weight. However, in some cases, a single dose of above 30 mg/Kg body weight or below 0.001 mg/Kg may also be used.

SPECIFIC MODES FOR CARRYING OUT THE INVENTION

Figure 1:
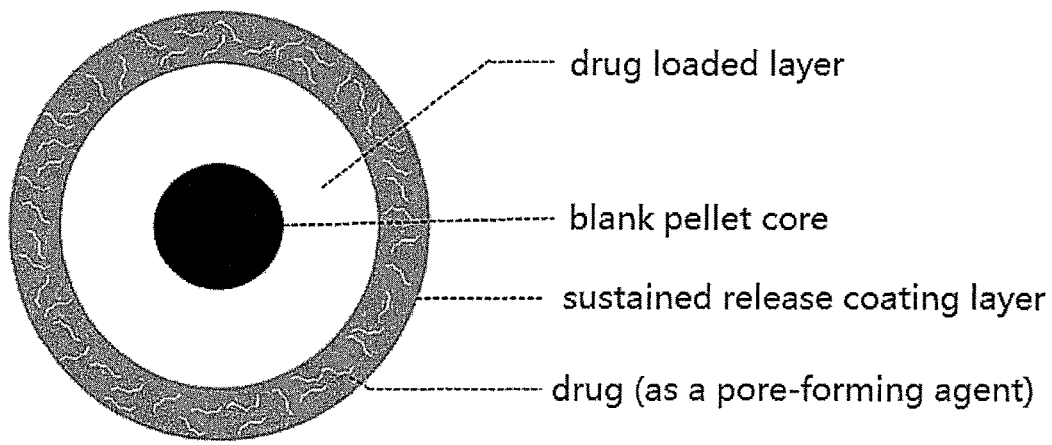
FIG. 1 illustrates the structure of the sustained-release pellet according to the invention.

The embodiments of the invention are described in detail by reference to the following examples. However, it is understood by those skilled in the art that the following examples are used only for the purpose of illustrating the invention, rather than limiting the protection scope of the invention. When the conditions are not indicated in the Examples, the Examples are carried out under the conventional conditions or the conditions recommended by the manufacturers. The reagents or instruments used in the present invention, the manufacturers of which are not indicated, are the commercially available conventional products.

Unless otherwise specified, the parameters in the following embodiments are calculated as follows.

Drug-loading percentage of pellet (%)=
$(W_{total\ weight\ of\ pellet} - W_{weight\ of\ blank\ pellet\ core})/W_{weight\ of\ raw\ material\ drug} \times 100\%$;

Weight gain caused by sustained-release coating (%)=
$(W_{total\ weight\ of\ pellet\ after\ sustained-release\ coating} - W_{total\ weight\ of\ pellet\ before\ sustained-release\ coating})/W_{total\ weight\ of\ pellet\ after\ sustained-release\ coating} \times 100\%$;

Adhesion rate of pellet=
$(W_{total\ weight\ of\ pellet\ after\ sustained-release\ coating} - W_{total\ weight\ of\ not\ adhered\ pellet})/W_{total\ weight\ of\ pellet\ after\ sustained-release\ coating} \times 100\%$.

In the Examples of sustained-release pellets according to the invention, unless otherwise specified, the following methods are used in measurement. According to the first method (for use in sustained-release preparations or controlled-release preparations) of determination methods for release rate (Append. X D) in Chinese Pharmacopoeia (2010) Part II Appendix, the device of the second method (stirring paddle method) of determination methods for dissolution rate (Append. X C) in Chinese Pharmacopoeia (2010) Part II Appendix is used, water is used as dissolution medium, e.g., 500 ml water is used as dissolution medium of metoprolol succinate, or 1000 ml water is used as dissolution medium of hydrochlorothiazide, the temperature was set at 37° C., the rotation speed was set at 100 r/min, samples are taken at specified different time points (meanwhile an equal amount of medium is supplemented), and filtrated to obtain filtrates, and the filtrates are taken as test solutions and analyzed.

The drug content of a sustained-release pellet comprising metoprolol is analyzed spectrophotometrically at 274 nm (Chinese Pharmacopoeia (2010) Part II Appendix IV A). Metoprolol succinate reference substance (purchased from market, USP standard reference substance) is measured by the same method, and cumulative released percentages of drug at different time points are calculated.

The drug content of a pharmaceutical composition granule comprising hydrochlorothiazide is analyzed spectrophotometrically at 274 nm (Chinese Pharmacopoeia (2010) Part II Appendix IV A). Hydrochlorothiazide reference substance is measured by the same method, and cumulative released percentages of drug at different time points are calculated.

Example 1

800 g metoprolol succinate as raw material was weighed, and 1350 ml water was added to obtain a mixure. The resultant mixture was stirred and dissolved under heating, to obtain a drug-containing coating solution.

200 g sucrose pellet cores, 200 g starch pellet cores and 200 g microcrystalline cellulose pellet cores with a particle size of 200 μm~350 μm were weighed, and were placed in a bottom-spray coating pan of fluidized bed to perform coating, respectively, wherein the temperature of air intake temperature was set at 70° C. to keep the temperature in the pan at 50±2° C., the pressure of air intake was set at 0.35 bar, the pressure of atomization was set at 1.5 bar, and the rate of liquid-spraying was set at 5~15 g/min (the rate of liquid-spraying could be adjusted depending on fluidized state). When the blank pellet cores were at a fluidized state, the drug-containing coating solution was bottom-sprayed onto the surface of blank pellet cores to perform drug loading. After drug loading was finished, the fluidized state was further kept at 70° C. for 5 min, to obtain metoprolol succinate loaded pellets with different particle sizes. The metoprolol succinate loaded pellets were passed through an 80 mesh screen and a 40 mesh screen, respectively, to discard fine power and adhered pellets, then weighed. The total weight of the drug-loading pellets, i.e., $W_{total\ weight\ of\ pellet}$, was recorded, and the drug-loading percentage and adhesion rate of the drug loaded pellets were calculated. The results were shown in Table 1.

TABLE 1

Results on coating and drug-loading of different blank pellet cores

| Formula | Investigation indexes | | |
|---|---|---|---|
| | Drug-loading percentage of pellet (%) | Drug-loading time (min) | Adhesion rate (%) |
| Formula 1 (sucrose pellet core) | 84.8 | 263 | 8.9 |
| Formula 2 (starch pellet core) | 95.7 | 205 | 3.1 |
| Formula 3 (microcrystalline cellulose pellet core) | 95.8 | 190 | 2.8 |

Example 2

Formula

Formula of drug loaded pellet (drug sustained-release part) was as following:
metoprolol succinate (g): 800;
sucrose pellet core (200~350 μm) (g): 200.

Formula of sustained-release coating layer (rapid-release part) was as following:

| Formula (No.) | Ethyl cellulose (10 cps) (g) | Metoprolol succinate (g) |
|---|---|---|
| Formula 4 | 200 | 60 |
| Formula 5 | 200 | 40 |
| Formula 6 | 200 | 20 |

Preparation method was as follows.

(1) 800 g metoprolol succinate as raw material (synthesized by the processes described in the paper, Jiangxi Chemical Industry, 2003(1): 4-6) was weighed, and 1350 ml water was added to obtain a mixture. The resultant mixture was stirred and dissolved under heating at 60° C.~70° C., and passed through a 200 mesh screen, to obtain a drug-containing coating solution.

200 g sucrose pellet cores with a particle size of 200 μm~350 μm were weighed, and placed in a bottom-spray coating pan of fluidized bed to perform coating, wherein the temperature of air intake temperature was set at 70° C. to keep the temperature in the pan at 50±2° C., the pressure of air intake was set at 0.35 bar, the pressure of atomization was set at 1.5 bar, and the rate of liquid-spraying was set at 5~15 g/min (the rate of liquid-spraying could be adjusted depending on fluidized state). When the sucrose pellet cores were at a fluidized state, the drug-containing coating solution was bottom-sprayed onto the surface of sucrose pellet cores to perform drug loading. After drug loading was finished, the fluidized state was further kept at 70° C. for 5 min, and the resultant pellets were passed through an 80 mesh screen and a 40 mesh screen, respectively, to discard fine power and adhered pellets. Metoprolol succinate loaded pellets were obtained.

(2) Ethyl cellulose (EC) at an amount as described in the above formula was weighed, and dissolved by adding a suitable amount of 95% ethanol, and metoprolol succinate at an amount as described in the above formula was then added and dissolved to obtain a sustained-release coating solution.

(3) 500 g of each of the above obtained metoprolol succinate loaded pellets was weighed, and placed in a bottom-spray coating pan of fluidized bed to perform coating, respectively, wherein the temperature of air intake was set at 40~45° C. to keep the temperature in the pan at 30~35° C., the pressure of air intake was set at 0.35 bar, the pressure of atomization was set at 1.5 bar, and the rate of liquid-spraying was set at 3~12 g/min. When the drug loaded pellets were at a fluidized state, the above obtained three kinds of sustained-release coating solutions according to Formula 4, Formula 5 or Formula 6 were bottom-sprayed onto the surface of drug loaded pellets, respectively, to obtain sustained-release pellets containing metoprolol succinate, wherein the weight gains thereof cause by the sustained-release coatings were 33.1%, 31.6%, and 30.8%, which were corresponding to Formula 7, 8, and 9 in Table 2, respectively.

The drug cumulative released percentages of the obtained sustained-release pellets containing metoprolol succinate were measured and shown in Table 2.

TABLE 2

The results on cumulative released percentage of the sustained-release pellets containing ethyl cellulose (EC) and metoprolol succinate at different ratios

| Formula | Cumulative released percentage (%) | | | | | |
|---|---|---|---|---|---|---|
| | 1 h | 4 h | 8 h | 12 h | 16 h | 20 h |
| Formula 7 | 17.1 | 44.5 | 72.5 | 92.4 | 99.1 | 100.4 |
| Formula 8 | 13.5 | 38.2 | 65.4 | 85.1 | 95.5 | 100.2 |
| Formula 9 | 11.8 | 35.6 | 60.9 | 81.1 | 90.7 | 98.2 |

Example 3

500 g metoprolol succinate loaded pellets prepared by the method of Example 2 were subjected to sustained-release coating. The coating process was the same as the one in Example 2. As calculated based on the consumed volume of the coating solution, the sustained-release pellets having different weight gains caused by sustained-release coating (when the coating solution was consumed completely, the weight gain caused by coating was 40%) were obtained. Their drug cumulative released percentages were shown in Table 3.

Formula of sustained-release coating layer was as following:
ethyl cellulose (10 cps)(g): 200;
metoprolol succinate (g): 45.

TABLE 3

Evaluation results on cumulative released percentages of the sustained-release pellets having different coating weight gains

| Formula | Weight gain caused by sustained-release coating (%) | cumulative released percentage (%) | | | |
|---|---|---|---|---|---|
| | | 1 h | 4 h | 8 h | 20 h |
| Formula 10 | 20 | 25.4 | 52.6 | 85.7 | 99.9 |
| Formula 11 | 25 | 21.2 | 46.9 | 75.1 | 99.3 |
| Formula 12 | 35 | 16.1 | 40.7 | 63.5 | 98.7 |
| Formula 13 | 40 | 14.2 | 33.9 | 56.4 | 95.6 |

Example 4

500 g metoprolol succinate loaded pellets prepared by the method of Example 2 were subjected to sustained-release coating. The coating process was the same as the one in Example 2. The formula of the sustained-release coating was as followed. As calculated based on the consumed volume of the coating solution, the sustained-release pellets having different weight gains caused by sustained-release coating were obtained. Their drug cumulative released percentages were shown in Table 4.

Formula of sustained-release coating layer was as following:

ethyl cellulose (10 cps)(g): 200;
metoprolol succinate (g): 25;
hydroxypropyl cellulose (Klucel LF) (g): 20.

TABLE 4

Evaluation results on cumulative released percentages of the sustained-release pellets having different coating weight gains

| Formula | Weight gain caused by sustained-release coating (%) | Cumulative released percentage (%) | | | |
|---|---|---|---|---|---|
| | | 1 h | 4 h | 8 h | 20 h |
| Formula 14 | 20 | 20.7 | 45.9 | 74.3 | 96.6 |
| Formula 15 | 25 | 16.1 | 40.5 | 62.2 | 95.9 |
| Formula 16 | 35 | 12.2 | 31.3 | 52.4 | 91.4 |
| Formula 17 | 40 | 10.1 | 27.6 | 50.4 | 87.5 |

Example 5

Experiment on Reproducibility of Method for Preparing Metoprolol Succinate Loaded Pellet 800 g metoprolol succinate as raw material was weighed, and 1350 ml water was added to obtain a mixture. The resultant mixture was stirred and dissolved under heating at 60° C.~70° C., and passed through a 200 mesh screen, to obtain a drug-containing coating solution.

200 g sucrose pellet cores with a particle size of 200 μm~350 μm were weighed, and placed in a bottom-spray coating pan of fluidized bed to perform coating, wherein the temperature of air intake was set at 70° C. to keep the temperature in the pan at 50±2° C.), the pressure of air intake was set at 0.35 bar, the pressure of atomization was set at 1.5 bar, and the rate of liquid-spraying was set at 5~15 g/min (the rate of liquid-spraying could be adjusted depending on fluidized state). When the sucrose pellet cores were at a fluidized state, the drug-containing coating solution was bottom-sprayed onto the surface of sucrose pellet cores to perform drug loading. After drug loading was finished, the fluidized state was further kept at 70° C. for 5 min, and the resultant pellets were passed through an 80 mesh screen and a 40 mesh screen, respectively, to discard fine powder and adhered pellets. The metoprolol succinate loaded pellets were obtained and weighed. The total weight of pellets after drug loading, i.e., $W_{total\ weight\ of\ pellets}$, was recorded, and the drug-loading percentage and yield of pellets were calculated, as shown in Table 5.

TABLE 5

Results on reproducibility of method for preparing metoprolol succinate loaded pellets

| Sample batch | Preparation scale (preparation unit/batch) | Amount of main drug (g/batch) | Amount of sucrose pellet core (g/batch) | Amount of drug loaded pellets (g/batch) | Drug-loading percentage (%) | Yield (%) |
|---|---|---|---|---|---|---|
| 1 | 16800 | 800 | 200 | 964 | 95.5 | 96.4 |
| 2 | 16800 | 800 | 200 | 962 | 95.2 | 96.2 |
| 3 | 16800 | 800 | 200 | 963 | 95.3 | 96.3 |

Note:
the metoprolol succinate dose per unit of preparation is 47.5 mg;
the yield is the amount of drug loaded pellets divided by the total amount of raw materials.

Example 6

Experiment on Reproducibility of Method for Preparing Sustained-Release Pellet Comprising Metoprolol Succinate 200 g ethyl cellulose (10 cps) was weighed, and a suitable amount of 95% ethanol was added to obtain a mixture. The resultant mixture was stirred and dissolved under heating at 40° C.-50° C. About 50 g metoprolol succinate was added, and the resultant mixture was stirred and dissolved under heating at 40° C.-50° C. 95% ethanol was added to a final volume of 2152 ml, to obtain a sustained-release coating solution.

Figure 2:
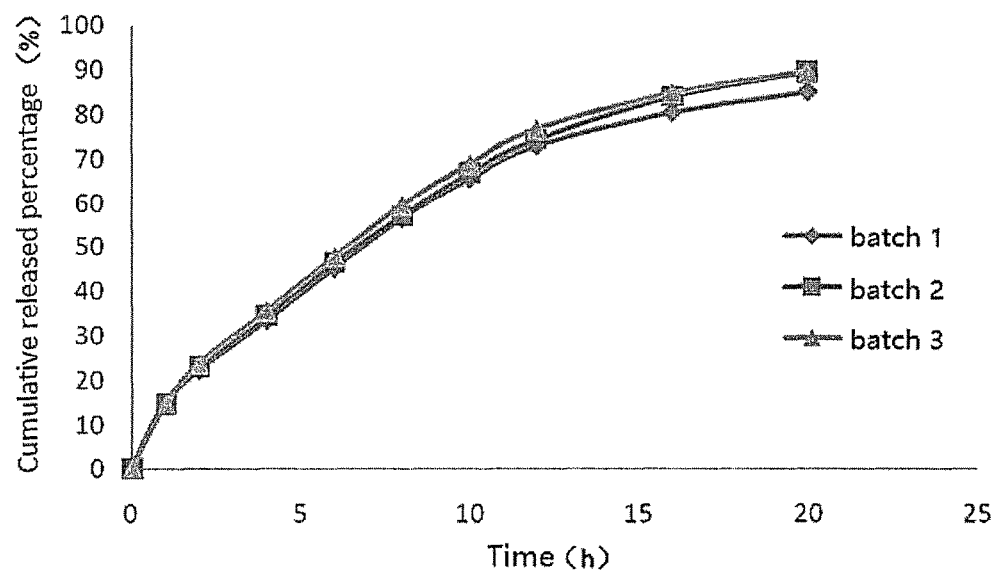
FIG. 2 illustrates the experiment on reproducibility of release curves of sustained-release pellets comprising metoprolol succinate in different batches in Example 6.

500 g metoprolol succinate loaded pellets prepared in Example 5 were placed in a bottom-spray coating pan of fluidized bed to perform coating, wherein the temperature of air intake was set at 40~45° C. to keep the temperature in the pan at 30~35° C.) the pressure of air intake was set at 0.35 bar, the pressure of atomization was set at 1.5 bar, and the rate of liquid-spraying was set at 3~12 g/min. When the drug loaded pellets were at a fluidized state, the sustained-release coating solution was bottom-sprayed onto the surface of metoprolol succinate loaded pellets, to obtain three batches of sustained-release pellets comprising metoprolol succinate, which had the weight gain caused by sustained-release coating of 32.1%, 31.8%, and 32.0%, respectively. The results were shown in Table 6. The release curves were shown in FIG. 2.

TABLE 6

Experimental results on reproducibility of method for preparing sustained-release coating pellets comprising metoprolol succinate

| Sample batch | Amount of drug loaded pellets (g/batch) | Amount of ethyl cellulose (g/batch) | Amount of succinate metoprolol (g/batch) | Sustained-release pellet comprising metoprolol (g/batch) | Yield (%) | Cumulative released percentage (%) | | | |
|---|---|---|---|---|---|---|---|---|---|
| | | | | | | 1 h | 4 h | 8 h | 20 h |
| 1 | 500 | 200 | 46 | 736 | 98.7 | 12.4 | 39.2 | 68.5 | 99.4 |
| 2 | 500 | 200 | 46 | 733 | 98.3 | 13.1 | 41.6 | 69.5 | 99.8 |
| 3 | 500 | 200 | 46 | 735 | 98.5 | 12.9 | 39.1 | 68.8 | 99.4 |

Example 7

Experiment on Release Difference of Unit Preparations

Sustained-release pellets comprising metoprolol succinate prepared in Example 6 were filled into vacant gelatin capsules, to obtain sustained-release capsules comprising metoprolol succinate.

Sustained-release pellets comprising metoprolol succinate of Formula 13 in Example 3, were homogeneously mixed with an equal amount of microcrystalline cellulose (PH102 type), and 0.3% sodium fumaryl stearate as lubricant was then added, then mixed well. The resultant mixture was pressed into tablets with a hardness of 10 kg-15 kg, to obtain sustained-release tablets comprising metoprolol succinate.

18 sustained-release capsules comprising metoprolol succinate and 18 sustained-release tablets comprising metoprolol succinate as prepared above were determined for their drug cumulative released percentages, and their relative standard deviation (RSD) was calculated. The results were shown in Table 7.

TABLE 7

Evaluation results on cumulative released percentages of sustained-release capsule comprising metoprolol succinate and sustained-release tablet comprising metoprolol succinate

| Sampling time (h) | Sustained-release capsule comprising metoprolol succinate | | Sustained-release tablet comprising metoprolol succinate | |
|---|---|---|---|---|
| | Cumulative released percentage (%) | RSD (%) | Cumulative released percentage (%) | RSD (%) |
| 1 | 11.6 | 4.7 | 12.3 | 18.6 |
| 4 | 38.7 | 3.2 | 40.5 | 9.4 |
| 8 | 62.7 | 1.1 | 65.4 | 6.8 |
| 12 | 85.7 | 1.5 | 86.9 | 4.6 |
| 16 | 93.7 | 0.8 | 94.1 | 4.2 |
| 20 | 99.8 | 1.2 | 100.7 | 4.9 |

Example 8

Formula 18

Formula of drug loaded pellets (sustained-release part) was as following:

metoprolol succinate (g): 770;

microcrystalline cellulose (g): 200;

hypromellose (g): 1.

Formula of sustained-release coating layer (immediate-release part) was as following:

ethyl cellulose (10 cps)(g): 200;

metoprolol succinate (g): 30.

Preparation Method:

(1) 770 g metoprolol succinate passed through an 80 mesh screen was weighed, and homogeneously mixed with 180 g microcrystalline cellulose, then prepared into a suitable soft material with about 33 mL of 3% (W/V) hypromellose (HPMC) aqueous solution used as adhesive. The soft material was placed in a machine of extruding and round as ball to prepare pellets, wherein the speed of extruding was set at 30 rpm, the speed of round was set at 350 rpm, and the time for round as ball was 5 min. The prepared pellets were dried in an oven at 40° C. for 4 h, and screened to obtain the target pellets having a particle size of 400~550 μm, i.e., metoprolol succinate loaded pellets.

(2) Ethyl cellulose (EC) at an amount as described in the above formula was weighed, and dissolved by adding a suitable amount of 95% ethanol, then metoprolol succinate at an amount as described in the above formula was added and dissolved to obtain a sustained-release coating solution.

500 g above prepared metoprolol succinate loaded pellets were placed in a bottom-spray coating pan of fluidized bed to perform coating, wherein the temperature of air intake was set 40~45° C. to keep the temperature in the pan at 30~35° C., the pressure of air intake was set at 0.35 bar, the pressure of atomization was set at 1.5 bar, and the rate of liquid-spraying was set at 3~12 g/min. When the drug loaded pellets were at a fluidized state, above prepared sustained-release coating solution was bottom-sprayed onto the surface of metoprolol succinate loaded pellets, to obtain sustained-release pellets comprising metoprolol succinate.

The determined results on drug cumulative released percentage of the prepared sustained-release pellets comprising metoprolol succinate were shown in Table 8.

TABLE 8

Evaluation results on cumulative released percentage of sustained-release pellets comprising metoprolol succinate

| Sampling time | Cumulative released percentage (%) |
|---|---|
| 1 h | 11.2 |
| 4 h | 31.8 |
| 8 h | 56.5 |
| 12 h | 78.4 |
| 16 h | 95.5 |
| 20 h | 99.7 |

Example 9

Pharmaceutical Composition Granules Comprising Hydrochlorothiazide Prepared by Melt Method Formula 19 was as following:
hydrochlorothiazide (g): 250;
microcrystalline cellulose (g): 375 g;
polyethylene glycol 6000 (g): 375 g.

Preparation Method:

hydrochlorothiazide was homogenously mixed with microcrystalline cellulose at an amount as described in the above formula to obtain a mixture. polyethylene glycol 6000 at an amount as described in the above formula was melted at 70° C., the mixture of hydrochlorothiazide and microcrystalline cellulose was added, then stirred homogeneously and immediately passed through a 20 mesh screen, to get the final product.

Example 10

Pharmaceutical Composition Granules Comprising Hydrochlorothiazide Prepared by Hot-Melt Extrusion Method Formula 20 was as following:
hydrochlorothiazide (g): 150;
PVP-VA 64 (g): 350.

Preparation Method:

a hot-melt extruder was set at 180° C. for each region, at a speed of 25 rpm, and balanced for 30 min. Hydrochlorothiazide at an amount as described in the above formula was homogenously mixed with PVP-VA64 at an amount as described in the above formula, and placed in a loading hopper of the hot-melt extruder, then extruded into a shape of bar from the die hole after 1 min, caught in a stainless steel disc, left at room temperature for 4 h, and then crushed and passed through a 30 mesh screen, to obtain the final product.

Example 11

Comparison of Dissolution Rate of Pharmaceutical Compositions Comprising Hydrochlorothiazide A suitable amount of pharmaceutical compositions comprising hydrochlorothiazide of Formula 19 and Formula 20 (corresponding to 10 mg hydrochlorothiazide) was weighed, respectively. According to the second method (stirring paddle method) for dissolution test (Append. □C) in Chinese Pharmacopoeia (2010) Part II Appendix, 1000 ml water was used as dissolution medium, and dissolution rates were determined at different time points at 37° C., and under a speed of 50 r/min. 5 mL samples were taken at 5 min, 15 min, 30 min, 45 min and 60 min (meanwhile an equal amount of medium was supplemented), and filtrated to obtain a filtrate, and the filtrates are taken as test samples. Ultraviolet spectrophotometry (Chinese Pharmacopoeia (2010) Part II Appendix □A) was used to determine absorbance at a wavelength of 272 nm. Hydrochlorothiazide reference substance was measured by the same method, and cumulative released percentages of the main drug hydrochlorothiazide at different time points were calculated by external standard method. The dissolution rates of pharmaceutical compositions comprising hydrochlorothiazide of Formula 19 and Formula 20 were shown in Table 9.

TABLE 9

Cumulative released percentage of pharmaceutical compositions comprising hydrochlorothiazide of different formulas

| Formula No. | Cumulative released percentage (%) | | | | |
|---|---|---|---|---|---|
| | 5 min | 15 min | 30 min | 45 min | 60 min |
| Formula 19 | 5.5 | 8.9 | 13.7 | 45.6 | 56.7 |
| Formula 20 | 15.6 | 30.4 | 56.3 | 62.5 | 75.7 |

Example 12

Preparation of Metoprolol Succinate Sustained-Release/Hydrochlorothiazide Capsules The sustained-release pellets comprising metoprolol succinate prepared in Example 6, and pharmaceutical composition comprising hydrochlorothiazide prepared in Example 9, as calculated on basis of their contents, were mixed at a certain weight ratio, and filled into capsules, wherein each capsule contained 47.5 mg metoprolol succinate and 12.5 mg hydrochlorothiazide.

Example 13

Preparation of Metoprolol Succinate Sustained-Release/Hydrochlorothiazide Capsules The sustained-release pellets comprising metoprolol succinate prepared in Example 8, and the pharmaceutical composition comprising hydrochlorothiazide prepared in Example 10, as calculated on basis of their contents, were mixed at a certain weight ratio, and filled into capsules, wherein each capsule contained 47.5 mg metoprolol succinate and 12.5 mg hydrochlorothiazide.

Comparative Example 1

Formula 21:
Formula of metoprolol succinate loaded pellet was as following:
metoprolol succinate (g): 800;
blank sucrose pellet core (200~350 μm) (g): 200.
Formula of sustained-release layer was as following:
ethyl cellulose (10 cps) (g): 200;
hydroxypropyl cellulose (Klucel LF) (HPC) (g): 30.

Preparation Method:

(1) 800 g metoprolol succinate as raw material was weighed, and 1350 ml water was added to obtain a mixture. The resultant mixture was stirred and dissolved under heating at 60° C.-70° C., and passed through a 200 mesh screen, to obtain a drug-containing coating solution.

200 g sucrose pellet cores with a particle size of 200 μm~350 μm were weighed, and placed in a bottom-spray coating pan of fluidized bed to perform coating, wherein the temperature of air intake was set at 70° C. to keep the temperature in the pan at 50±2° C., the pressure of air intake was set at 0.35 bar, the pressure of atomization was set at 1.5 bar, and the rate of liquid-spraying was set at 5~15 g/min (the rate of liquid-spraying could be adjusted depending on fluidized state). When the sucrose pellet cores were at a fluidized state, the drug-containing coating solution was bottom-sprayed onto the surface of sucrose pellet cores to perform drug loading. After drug loading was finished, the fluidized state was further kept at 70° C. for 5 min, and passed through an 80 mesh screen and a 40 mesh screen, respectively, to discard fine powder and adhered pellets, and metoprolol succinate loaded pellets were obtained.

(2) Ethyl cellulose (EC) at an amount as described in the above formula was weighed, and dissolved by a suitable amount of 95% ethanol, and then hydroxypropyl cellulose (HPC) at an amount as described in the above formula was added and dissolved to obtain a sustained-release coating solution.

(3) 500 g above prepared metoprolol succinate loaded pellets were weighed, and placed in a bottom-spray coating pan of fluidized bed to perform coating, wherein the temperature of air intake was set at 40~45° C. to keep the temperature in the pan at 30~35° C., the pressure of air intake pressure was set at 0.35 bar the pressure of atomization pressure was set at 1.5 bar and the rate of liquid-spraying was set at 3~12 g/min. When the drug loaded pellets were at a fluidized state, above prepared sustained-release coating solution was bottom-sprayed onto the surface of drug loaded pellets, to obtain sustained-release pellets comprising metoprolol succinate.

Experimental Example 1

Figure 3:
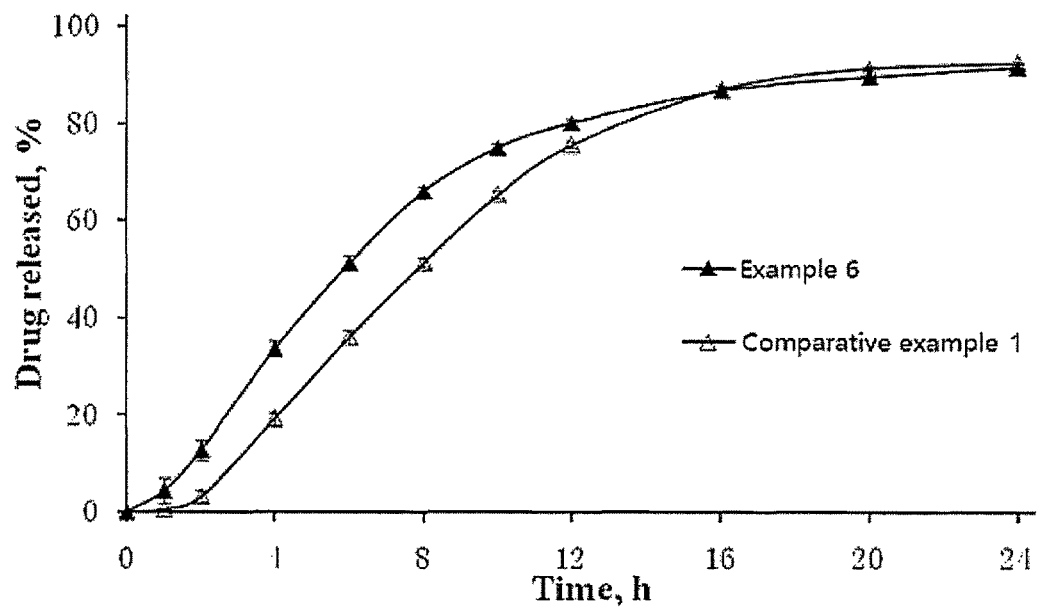
FIG. 3 illustrates the comparison of release rate between the sustained-release pellet (in which the sustained-release film comprises the active constituent metoprolol succinate) prepared in Example 6 and the sustained-release pellet (in which sustained-release film comprises no active constituent metoprolol succinate) prepared in Comparative example 1.

The sustained-release pellets prepared in Example 6, and the sustained-release pellets prepared in Comparative example 1 were taken. In accordance with the first method (for use in sustained-release preparations or controlled-release preparations) of determination methods for release rate (Append. □D) in Chinese Pharmacopoeia (2010) Part II Appendix, the device of the second method (stirring paddle method) of determination methods for dissolution test (Append. □C) in Chinese Pharmacopoeia (2010) Part II Appendix was used, 500 ml water was used as dissolution medium, the temperature was set at 37° C., the rotation speed was set at 100 r/min, and samples were taken at different time points (meanwhile an equal amount of medium was supplemented), and filtrated to obtain filtrates. The filtrates were taken as test samples. Ultraviolet spectrophotometry (Chinese Pharmacopoeia (2010) Part II Appendix □A) was used to determine absorbance at a wavelength of 274 nm. Metoprolol succinate reference substance was measured by the same method, and cumulative released percentages of the drug at different time points were calculated. The results were shown in Table 10 and FIG. 3.

TABLE 10

Evaluation results on cumulative released percentage of sustained-release pellets comprising metoprolol succinate

| | Cumulative released percentage (%) | |
|---|---|---|
| Time (h) | Formula of Comparative example 1 | Formula of Example 6 |
| 1 | 0.70 | 4.50 |
| 2 | 3.32 | 12.82 |
| 4 | 19.20 | 33.61 |
| 6 | 36.06 | 51.21 |
| 8 | 51.23 | 65.91 |
| 10 | 65.25 | 74.93 |
| 12 | 75.62 | 80.12 |
| 16 | 87.09 | 86.95 |
| 20 | 91.41 | 89.79 |
| 24 | 92.56 | 91.68 |

The results showed that the sustained-release pellets prepared by the present technical solution (Example 6) had the release rate increased significantly within 2 h compared to the pellets prepared by the traditional method (Comparative example 1), and eliminated the lagging phase brought about by the traditional preparation process.

Experimental Example 2

Pharmacokinetic Study on Sustained-Release Pellets Comprising Metoprolol Succinate in Beagle Dogs Six beagle dogs were used in double periodic, randomized cross-over study design, and were orally administered once with an equal dose of experimental preparation (the sustained-release pellets comprising metoprolol succinate prepared in Example 6) and reference preparation (the sustained-release pellets comprising metoprolol succinate prepared in Comparative example 1), respectively. HPLC analytic method was used to determine the concentration of metoprolol succinate in blood plasma after administration. Data 9 processing was carried out by DAS2.0 program.

Result

Figure 4:
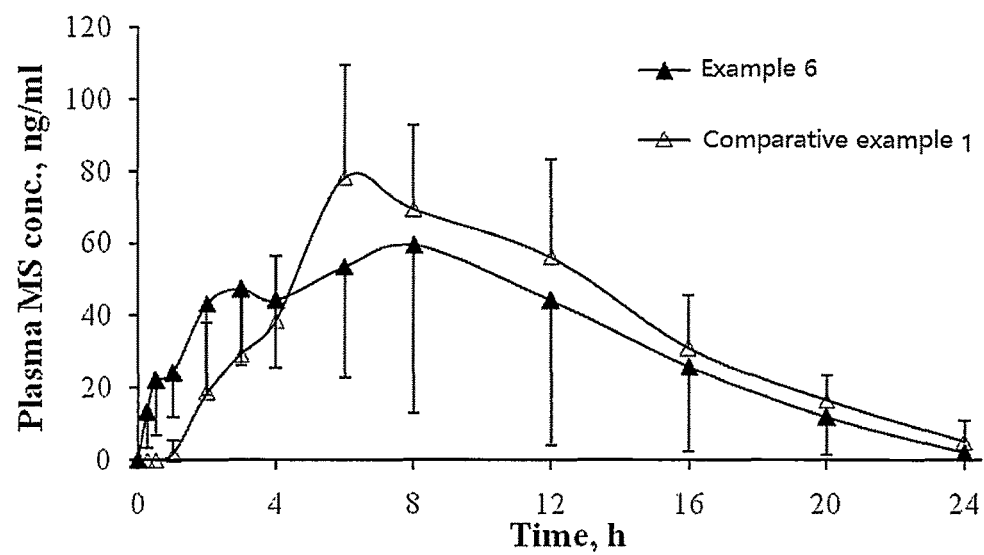
FIG. 4 illustrates the comparison of in vivo absorption dynamics between the sustained-release pellet (in which the sustained-release film comprises active constituent metoprolol succinate) prepared in Example 6 and the sustained-release pellet (in which the sustained-release film comprises no active constituent metoprolol succinate) prepared in Comparative example 1.

After single oral administration of an equal dose of the experimental preparation and the reference preparation of sustained-release pellets comprising metoprolol succinate (95 mg), the time to peak ($T_{max}$) was 0.92±0.58 h and 1.42±1.07 h, respectively; the peak concentration ($C_{max}$) was 79.87±19.98 ng·ml$^{-1}$ and 78.78±15.70 ng·ml$^{-1}$, respectively; the plasma clearance half-life ($T_{1/2\beta}$) was 5.60±5.82 h and 6.39±4.61 h, respectively; and $AUC_{0-t}$ was 563.34±203.46 ng·h·ml$^{-1}$ and 518.32±111.19 ng·h·ml$^{-1}$, respectively. The drug concentration-time curve was shown in FIG. 4.

Conclusion

Compared with the reference preparation, single oral administration of an equal dose of the experimental preparation of sustained-release pellet comprising metoprolol succinate has following characteristics: (1) the bioavailability thereof was 108.52%±25.34%, and (2) the time to peak thereof was about 30 min in advance.

It can be seen by comparison that the sustained-release pellets prepared by the present invention solves the problem concerning the phenomena of delayed release of the traditional pellets coated by ethyl cellulose and hydroxypropyl cellulose in vivo and in vitro. The method is simple in process and has good reproducibility, and its production parameter can be controlled easily, and therefore, the method is favorable for industrial production.

Although the embodiments of the invention are described in detail, a person skilled in the art would understand that according to all the already disclosed teachings, these details can be modified and replaced, and these alterations all fall in the protection scope of the invention. The scope of the invention is defined by the claims and any equivalent thereof.

What is claimed is:

1. A sustained-release composition consisting of a blank pellet core, an active constituent layer, and a sustained-release coating layer, characterized in that said active constituent layer consists of the active constituent and said sustained-release coating layer consists of the active constituent, a sustained release material, and optionally a pore-forming agent that is not the active constituent wherein said active constituent is selected from a free base of metoprolol, an optical isomer of metoprolol and a pharmaceutically acceptable salt of metoprolol, wherein the active constituent alone acts as a pore-forming agent, or the active constituent and the additional pore-forming substance co-act as a pore-forming agent, and, wherein the sustained-release material and the pore-forming agent in the sustained-release coating layer is in a weight ratio of from 1:0.1 to 1:0.4, and the active constituent and the additional pore-forming substance in the sustained-release coating layer, if present, is in a weight ratio of from 1:3 to 3:1.

2. The sustained-release composition according to claim 1, wherein said pharmaceutically acceptable salt of metoprolol is selected from the group consisting of metoprolol succinate, tartrate, fumarate, sorbate, laurate, and hydrochloride.

3. The sustained-release composition according to claim 1, wherein the sustained-release material is selected from the group consisting of a cellulose compound, Eudragit NE 30D, Eudragit RS 30D, Eudragit RL30D and a mixture thereof.

4. The sustained-release composition according to claim 1, wherein the sustained-release coating causes a weight gain of 20%~60% of the sustained-release composition.

5. The sustained-release composition according to claim 1, wherein the active constituent in the active constituent layer accounts for 40%-70% of the total weight of the sustained-release composition.

6. The sustained-release composition according to claim 1, wherein said blank pellet core is a sucrose pellet core.

7. The sustained-release composition according to claim 1, wherein said blank pellet core has a particle size of 200 μm~900 μm.

8. A method for preparing the sustained-release composition according to claim 1, comprising the following steps:
   1) dissolving the active constituent in a suitable amount of a solvent to obtain a drug solution, and coating a blank pellet core with the drug solution to obtain a drug loaded pellet, and
   2) dissolving a sustained-release coating material, the active constituent and optionally an additional pore-forming substance, as well as an adjuvant of the sustained-release coating layer adjuvant in a solvent to obtain a solution, and coating the drug loaded pellet obtained in the step 1) with the solution.

9. The method according to claim 8, wherein the solvent is selected from the group consisting of water, ethanol, propanol, propylene glycol, chloroform and a mixture thereof.

10. A pharmaceutical composition, comprising said sustained-release composition according to claim 1, and optionally a pharmaceutically acceptable carrier or excipient.

11. A combination product, comprising said sustained-release composition according to claim 1 and a pharmaceutical composition comprising hydrochlorothiazide.

12. The combination product according to claim 11, wherein said sustained-release composition and said pharmaceutical composition comprising hydrochlorothiazide can be capsulated into a capsule, or tableted into a tablet.

13. A method for treating a disease selected from hypertension, angina, myocardial infarction, hypertrophic cardiomyopathy, aortic dissection, arrhythmia, hyperthyreosis, or cardiac neurosis, comprising administering to a subject in need thereof a prophylactically or therapeutically effective amount of the sustained composition according to claim 1.

14. The sustained-release composition according to claim 1, wherein the additional pore-forming substance is hydroxypropyl cellulose.

15. A method for treating a disease selected from hypertension, angina, myocardial infarction, hypertrophic cardiomyopathy, aortic dissection, arrhythmia, hyperthyreosis, or cardiac neurosis, comprising administering to a subject in need thereof a prophylactically or therapeutically effective amount of the sustained composition according to claim 11.

16. The combination product according to claim 12, wherein said tablet is a conventional tablet, double-layer tablet, chewable tablet or orally disintegrating tablet.

17. The method according to claim 9, wherein said mixture is a mixture of water and ethanol.

* * * * *